(12) United States Patent
Willybiro et al.

(10) Patent No.: US 12,020,796 B2
(45) Date of Patent: Jun. 25, 2024

(54) INTRAVENOUS THERAPY SELECTION SYSTEM

(71) Applicant: Becton, Dickinson and Company, Franklin Lakes, NJ (US)

(72) Inventors: Kathryn Willybiro, Park City, UT (US); Huy Tran, Riverton, UT (US); Jacob Watts, Sandy, UT (US); Brian Douglas Roper, Pompton Plains, NJ (US); Yiping Ma, Layton, UT (US); Bart D. Peterson, Farmington, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 274 days.

(21) Appl. No.: 16/741,986

(22) Filed: Jan. 14, 2020

(65) Prior Publication Data

US 2020/0234812 A1 Jul. 23, 2020

Related U.S. Application Data

(60) Provisional application No. 62/794,432, filed on Jan. 18, 2019.

(51) Int. Cl.
*G16H 20/17* (2018.01)
*G16H 10/60* (2018.01)
*G16H 40/20* (2018.01)

(52) U.S. Cl.
CPC ............ *G16H 20/17* (2018.01); *G16H 10/60* (2018.01); *G16H 40/20* (2018.01)

(58) Field of Classification Search
CPC ......... G16H 10/60; G16H 20/17; G16H 40/20
See application file for complete search history.

(56) References Cited

U.S. PATENT DOCUMENTS

| 6,012,034 A * | 1/2000 | Hamparian ............ G16H 70/20 604/95.01 |
| 7,685,026 B1 | 3/2010 | McGrady et al. |
| 2002/0168618 A1 | 11/2002 | Anderson et al. |

(Continued)

FOREIGN PATENT DOCUMENTS

| JP | 2015512094 A | 4/2015 |
| WO | 99/05943 | 2/1999 |

(Continued)

*Primary Examiner* — Fonya M Long
*Assistant Examiner* — Anthony Balaj
(74) *Attorney, Agent, or Firm* — Kirton McConkie; Whitney Blair; Kevin Stinger

(57) ABSTRACT

An intravenous (IV) therapy selection system, may include a processor; a memory device to maintain an electronic medical record database comprising a plurality of medical records related to a plurality of patients; a clinician training module to provide training services and credentials to a plurality of clinicians; an IV therapy recommendation module to provide, via a display device, an IV device recommendation based on data descriptive of a first patient and a first clinician; and a placement location recommendation module to provide, via the display device, a recommendation on where to introduce the IV device into the first patient's body based on data descriptive of the first patient and the first clinician.

19 Claims, 6 Drawing Sheets

(56) References Cited

U.S. PATENT DOCUMENTS

| | | | |
|---|---|---|---|
| 2003/0216831 A1 | 11/2003 | Hart et al. | |
| 2011/0144658 A1 | 6/2011 | Wenderow | |
| 2012/0197619 A1* | 8/2012 | Namer Yelin | G16H 50/50 703/11 |
| 2012/0323597 A1* | 12/2012 | Woolford | G06Q 10/10 705/2 |
| 2013/0123974 A1* | 5/2013 | Clarke | G16H 20/13 700/236 |
| 2013/0173287 A1* | 7/2013 | Cashman | H04N 7/141 705/2 |
| 2014/0100551 A1* | 4/2014 | Holmstrom | A61M 25/01 604/517 |
| 2014/0356834 A1* | 12/2014 | Patrickson | G09B 23/288 705/317 |
| 2015/0227701 A1* | 8/2015 | Nicolaas | G16H 50/20 705/2 |
| 2015/0262512 A1 | 9/2015 | Rios et al. | |
| 2015/0332196 A1* | 11/2015 | Stiller | G06Q 10/06316 705/2 |
| 2016/0199230 A1* | 7/2016 | Doshi | A61F 13/84 156/219 |
| 2018/0225993 A1* | 8/2018 | Buras | A61B 8/06 |
| 2018/0308564 A1* | 10/2018 | Ross | G07C 9/00912 |
| 2018/0344308 A1 | 12/2018 | Nawana | |
| 2019/0206570 A1* | 7/2019 | Colister | G16H 10/60 |
| 2019/0388171 A1* | 12/2019 | Schermeier | G16H 40/63 |

FOREIGN PATENT DOCUMENTS

| | | |
|---|---|---|
| WO | 99/39315 | 8/1999 |
| WO | 02/070980 | 9/2002 |
| WO | 2010/068783 | 6/2010 |
| WO | 2018138345 A1 | 8/2018 |

* cited by examiner

INTRAVENOUS THERAPY SELECTION SYSTEM

RELATED APPLICATIONS

This application claims the benefit of U.S. Provisional Application No. 62/794,432, filed on Jan. 18, 2019, entitled "VASCULAR ACCESS CATHETER INTERFACE PLATFORM WITH VENDING CAPABILITY," which is incorporated herein in its entirety.

BACKGROUND

Catheters may be used throughout the medical community for a wide range of procedures and treatments. In specific examples, catheters may be used for a variety of infusion therapies. Catheters are used for infusing fluid, such as normal saline solution, various medicaments, and total parenteral nutrition, into a patient, withdrawing blood from a patient, or monitoring various parameters of the patient's vascular system. These types of catheters may be described as peripheral intravenous catheters (PIVCs).

A common type of PIVC is an over-the-needle PIVC. An over-the-needle PIVC is mounted over an introducer needle having a sharp distal tip. In this embodiment, the distal portion of the over-the-needle PIVC may tightly engage an outer surface of the needle to prevent peel-back of the catheter portion of the over-the-needle PIVC and thus facilitate insertion of the over-the-needle PIVC into the blood vessel. The over-the-needle PIVC and other types of PIVCs may often be used in a beside scenario with any number of clinicians or other health care providers (HCPs) using these PIVCs to administer medicaments and receive blood samples under the supervision of a doctor or other manager.

The process of placing a PIVC requires careful actuation by a clinician or other HCP to properly insert the PIVC into a plurality of systems in the patient's body. These systems may include the circulatory system, renal system, and digestive system, among other systems.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates to an intravenous (IV) therapy selection system. In some embodiments, an intravenous (IV) therapy selection system, including a processor; a memory device to maintain an electronic medical record database comprising a plurality of medical records related to a plurality of patients; a clinician training module to provide training services and credentials to a plurality of clinicians; an IV therapy recommendation module to provide, via a display device, an IV device recommendation based on data descriptive of a first patient and a first clinician; and a placement location recommendation module to provide, via the display device, a recommendation on where to introduce the IV device into the first patient's body based on data descriptive of the first patient and the first clinician.

In some embodiments, the intravenous therapy system includes a cart electrically coupled to the processor to receive input from the processor to open a drawer based on the IV device recommendation and recommendation on where to introduce the IV device into the first patient's body. In these embodiments, the opening of the drawer by the processor may increase security to the PIVC devices stored therein. In some embodiments, a locking module may be present to mechanically lock a plurality of draws of the cart to selectively prevent and provide access to the IV device by the clinician. In some embodiments, the cart further comprises an input device to receive input to the first clinician to record the use of the recommended IV and location of the introduction of the IV device.

In an embodiment, the intravenous therapy system may include a procedure module to provide the clinician with directions regarding how to introduce the IV device into the first patient's body. In this embodiment, the procedure module may present the directions audibly or visually. In some embodiments, the intravenous therapy selection system may include an IV logging module to track the use, stocking, and depletion of IV devices maintained within a cart electrically coupled to the processor.

The present disclosure also relates to a method of recommending a peripheral intravenous catheter (PIVC) and introduction location. In these embodiments, the method may include providing, at a display device, a PIVC recommendation to a first clinician among a plurality of clinicians via execution of a PIVC recommendation module by a processor, the PIVC recommendation being descriptive of which PIVC among a plurality of PIVC devices should be used in a medical procedure based on data descriptive of the first clinician a first patient among a plurality of patients; providing, at the display device, training and credentialing services to the first clinician; and providing, at the display device, an introduction location descriptive of where to introduce the PIVC device into the first patient's body based on data descriptive of the first patient and the first clinician.

In an embodiment, the method may include, subsequent to providing the PIVC recommendation, sending a signal to a locking device to open a drawer associated with and maintaining the PIVC recommended by the PIVC recommendation module. The method, in some embodiments, may also include receiving input from an input device descriptive of the use of the recommended IV by the first clinician and a location of the introduction of the IV device into the first patient's body. Receiving input from an input device, in an embodiment, may be descriptive of a level of successfulness of the introduction of the IV device into the first patient's body by the first clinician. In some embodiments, the method may also include executing, via the processor, an IV logging module to track the use, stocking, and depletion of IV devices maintained within a cart electrically coupled to the processor.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
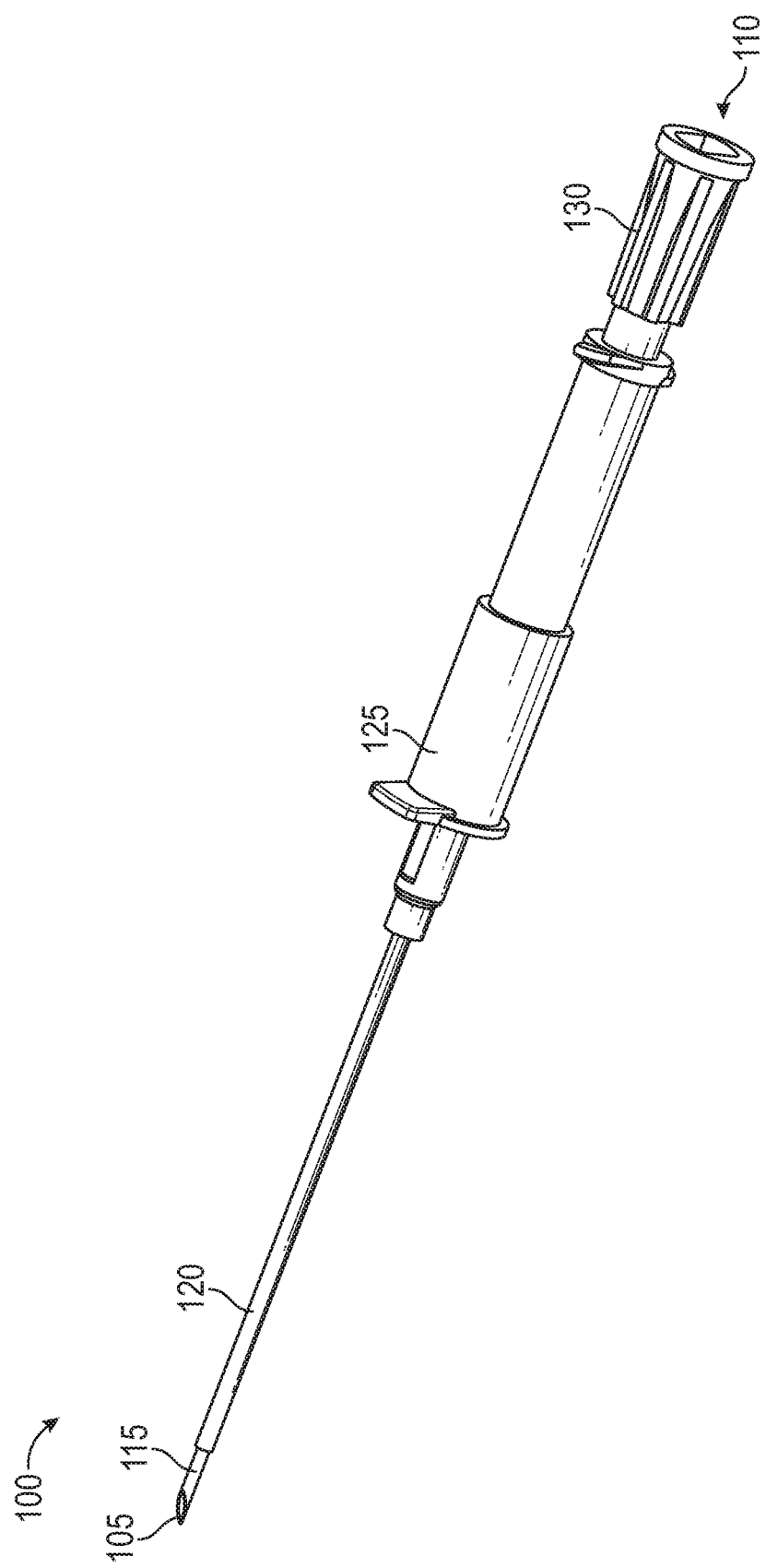
FIG. 1 is a perspective view of a peripheral intravenous catheter (PIVC) according to some embodiments of the present disclosure.

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

This invention is described herein using like reference numbers for like elements in the different embodiments. Although the embodiments described herein are used in connection with the use as an intravenous therapy system to receive a blood sample or introduce a medicament into the body of a patient, it is to be understood that the present specification contemplates that any type of catheter or medical instrument may be used besides the PIVC described herein. Consequently, while the embodiments of the intravenous (IV) therapy selection system are satisfied by embodiments in many different forms, there are shown in the drawings and herein described in detail, the embodiments described herein are presented merely as examples and are not meant to be limiting.

Referring now to FIG. 1, in some embodiments, the intravenous therapy selection system described herein may coordinate the use of a PIVC 100. The PIVC 100 presented in FIG. 1 is merely an example, and the present specification contemplates that any type of catheter may used in connection with the intravenous therapy selection system described herein. The PIVC 100 includes a sharp tip defined by a bevel at a distal end 105 with a proximal end 110 opposite the distal end 105 including a needle hub 130. The PIVC 100 may be formed from stainless steel in an embodiment. Materials that can be used to form the needle hub 130 include, but are not limited to, thermoplastic polymeric resins such as polycarbonate, polystyrene, polypropylene and the like. It is understood in the present disclosure, however, that other materials could be used to form needle hub 130 and PIVC 100.

The needle hub 130 may be formed with a coupling device such as a number of threads so that the needle hub 110 may be coupled to other medical instruments such as IV bladders full of a medicament, saline solution, or other type of fluid to be introduced into a patient's body.

The PIVC 100, may also include a barrel section 125 that is coupled to a catheter 120. the barrel section 125 may be of any length and may be a port through which the medicaments or other fluids, like blood, may pass from the needle 115 to the needle hub 110. The catheter 120 may be placed around the needle 115 and may run coaxial with the needle 115. In an embodiment, the length of the needle 115 may be greater than the length of the catheter 120 so that a portion of the needle 115 is exposed at the distal end 105 of the PIVC 100. This is done so that a distal tip of the needle 115 may have a bevel formed thereon and used to puncture the body of a patient during use.

Figure 2:
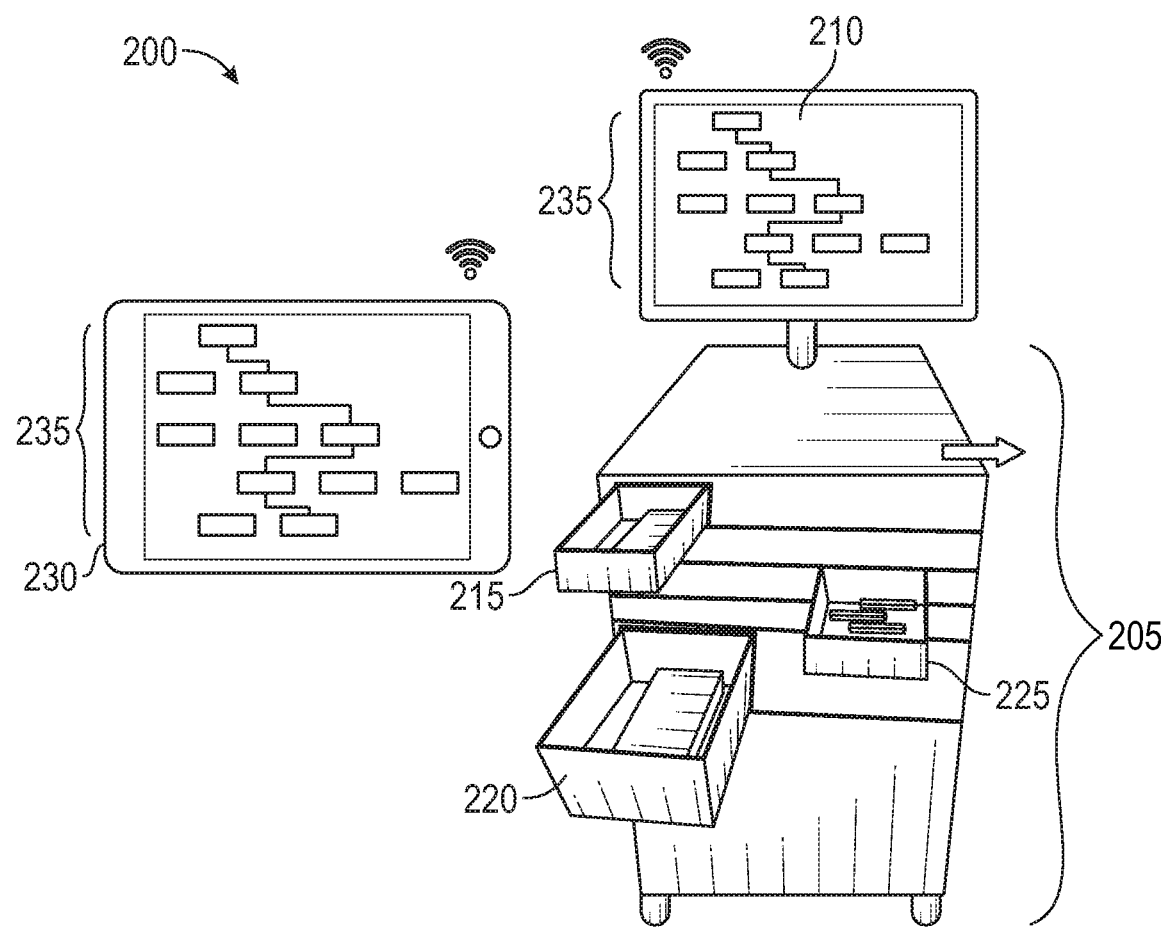
FIG. 2 is a graphical illustration of an intravenous therapy selection system according to some embodiments of the present disclosure.

FIG. 2 is a graphical illustration of an intravenous therapy selection system 200 according to some embodiments of the present disclosure. The intravenous therapy selection system 200 may be used to facilitate in a selection and placement location of a PIVC similar to, for example, that PIVC described in connection with FIG. 1. The present disclosure, however, contemplates that the intravenous therapy selection system 200 may be used to recommend any type of catheter and accompanying stabilizing devices, flushes, dressings, and kits used to administer medical care on a patient along with the PIVC 100.

The intravenous therapy selection system 200 may include, in an embodiment, a handheld display device such as a tablet 230. The tablet 230 may be used by a clinician or other HCP to initiate a decision-making process in order to determine which catheter (e.g., PIVC) device should be used on the patient as well as where on the patient's body the catheter is to be introduced into the patient's body. In a specific embodiment, the tablet 230 may provide a selectable decision tree 235 that guides the clinician to a selection of the IV device.

During operation the tablet 230 may access a number of databases used to help provide data to the decision tree 235 implemented by the user. By way of example, the tablet 230 may be communicatively coupled to a number of electronic medical records (EMRs) or electronic heath records (EHRs) maintained on an EMR database. The EMR database may include all maintained records regarding previous procedures a patient has received including any applications of an IV device. In a specific example, the EMR database may include the type of catheter used on the patient, the location where the catheter was introduced into the patients body, the clinician-perceived successfulness of the introduction of the catheter, the length that the catheter was present within the patient's body, and the type of procedure conducted with the catheter (e.g., blood draw, medicament infusion, etc.), among other details kept in such medical records. This information may be included with other patient-specific data such as a last recorded weight, results of blood tests, age, date of birth, and prior medical diagnosis, among other data.

During operation of the tablet 230 and after receipt of this patient-related data described, the tablet 230 may execute an IV therapy recommendation module to display the decision tree 235. In an embodiment, the decision tree 235 may be presented to the clinician with a number of decisions selected on the decision tree 235 based on the data accessed by the processor of the tablet 230 from the EMR database. In this embodiment, the clinician may visually review these preselected decisions to determine their accuracy and provide additional decision selections at the decision tree 235 if necessary. In an embodiment, any given preselection presented to the clinician on the decision tree 235 presented at the tablet 230 may be overridden by the clinician to arrive at another decision.

By way of example, the clinician may be presented with a patient that is to receive an IV catheter at a blood vessel in order to administer a medicament into the patient's blood stream. The clinician may obtain the tablet 230 and cause the processor of the tablet 230 to execute the IV therapy recommendation module. In an embodiment, due to the confidential nature of the information presented to the clinician, the execution of the IV therapy recommendation module may be done only after the clinician has presented credentials sufficient to gain access to the use of the tablet 230 such as a username and password or some other security key system.

Once the clinician has caused the processor to execute the IV therapy recommendation module, a graphical display presented to the user on the tablet 230 may request patient identification information that would allow the processor to access any and all medical records maintained on the EMR database. If and when any specific patient does not have any medical records recorded, the clinician may be presented with the decision tree 235 and may begin to select certain decisions on the decision tree in order to provide sufficient information to the processor executing the IV therapy recommendation module to provide a recommendation as to which type of IV catheter to use in order to administer to the patient the IV catheter at the blood vessel in order to administer a medicament into the patient's blood stream.

If and when medical records exist that are associated with the patient, the decision tree 235 may be presented to the clinician with, at least, preliminary decisions on the decision tree selected. These decisions may include, for example, a decision regarding which blood vessel to select in introducing the IV catheter into the patient's body. This decision may be made due to a medical record indicating that, within a given period, the patient had received an IV catheter at other blood vessels in the patient's body such that those other locations should not be used for a subsequent IV catheter insertion.

In addition to the EMR database records associated with the patient being used to form and make decisions on the decision tree, other factors may be used to form the decisions presented to the clinician in the decision tree 235 displayed on the tablet 230. For example, performance data related to the clinician may also be used. In this example, where the clinician is not entirely familiar with certain types of IV catheters, for example, the decision tree 235 may steer the clinician towards those IV catheters that the clinician is relatively more familiar with and has reported a successful introduction into a patient's body to the intravenous therapy selection system 200. The decision tree 235 may also include data relative to the clinician's training and qualifications to use certain types of IV catheters. As described herein, the clinician may have used the intravenous therapy selection system 200 to report successful achievement of certain clinical qualifications that indicate that the clinician is proficient in using a certain type of IV catheter. In this example, therefore, the decision tree 235 may include options associated with those qualifications and provide alternative IV catheters to use.

Still further, the IV therapy recommendation module may receive data at the processor regarding available IV catheters that are accessible by the clinician. In this embodiment, the intravenous therapy selection system 200 includes a cart 205 communicatively coupled to the tablet 230 that maintains a number of IV catheters therein. This cart 205 may include a number of drawers that hold specific types of IV catheters and accompanying stabilizing devices, flushes, dressings, and kits used to administer medical care on a patient along with the PIVC 100. The cart 205, in an embodiment, may include a processor and memory device so as to receive input from a clinician regarding a current stoke of IV catheters and accompanying stabilizing devices, flushes, dressings, and kits present within the cart 205. This data may be communicated to the processor of the tablet 230 to provide or eliminate IV catheter options at the decision tree 235. In an embodiment, the tablet 230 may be communicatively coupled to the cart 205 via a wired connection. In another embodiment, the tablet 230 may be communicatively coupled to the cart 205 via a wireless connection. In either embodiment, the data provided to the IV therapy recommendation module executed by the processor of the tablet 230 may be sufficient enough to provide a visual recommendation of which IV catheter to use at the display of the tablet 230.

After being provided with the IV catheter recommendation, the clinician may manually select an IV catheter among one or more potential IV catheters presented to the clinician at the tablet 230. In an embodiment, upon selection of an IV catheter at the tablet 230, a signal may be sent to a processor associated with the cart 205. The processor (not shown) may be communicatively coupled to a locking module that selectively locks and unlocks any number of drawers 215, 220, and 225 at the cart 205. Each of the drawers 215, 220, and 225 may hold therein an IV catheter and other stabilizing devices, flushes, dressings, and kits used to administer medical care on a patient and associated with the use of the IV catheter. In an embodiment, the cart 205 may include an IV catheter drawer 215, a flush drawer 225, and a start kit drawer 220. The start kit drawer 220 may be opened to allow the clinician to access stabilizing devices, swabs, and other devices used to prepare the location of the site where the IV catheter is to be introduced. The flush drawer 225 may be opened to allow the clinician to access a flushing device used to flush the IV catheter after insertion of the IV catheter into the patient's body. It is appreciated that more or less drawers may be unlocked and opened by the clinician selecting an IV catheter option on the tablet 230 based on the IV catheter chosen and medical care to be rendered to the patient.

In an embodiment, the cart 205 may include its own cart display device 210. The cart display device 210 may, similar to the tablet 230, present the decision tree 235 that is also presented on the tablet 230. Instead of using the tablet 230, the clinician may interface with the cart display device 210 to select an IV catheter to use and unlock those drawers 215, 220, and 225 associated with the chosen IV catheter and medical care to be conducted on the patient.

The tablet 230 as well as, or alternatively, the cart 205 may include a placement location recommendation module (not shown) that directs the clinician where to apply the IV catheter to the patient's body. As is described herein, the patient's history may be provided to the processors of the tablet 230 and cart 205 that identifies an appropriate location where to apply the IV catheter based, at least, on past IV catheter use at the patient's body.

In any embodiment, the tablet 230 and cart 205 may receive data from the clinician after the deployment of the IV catheter at the patient's body. This additional information may include a confirmation of the use of the IV catheter, the location or attempted locations on the patient's body the clinician had applied the IV catheter, and an indication from the clinician as to the level of successfulness of the introduction of the IV device into the first patient's body. This information may be recorded on the patient's individual EMRs for future reference again by the systems and methods described herein.

Figure 3:
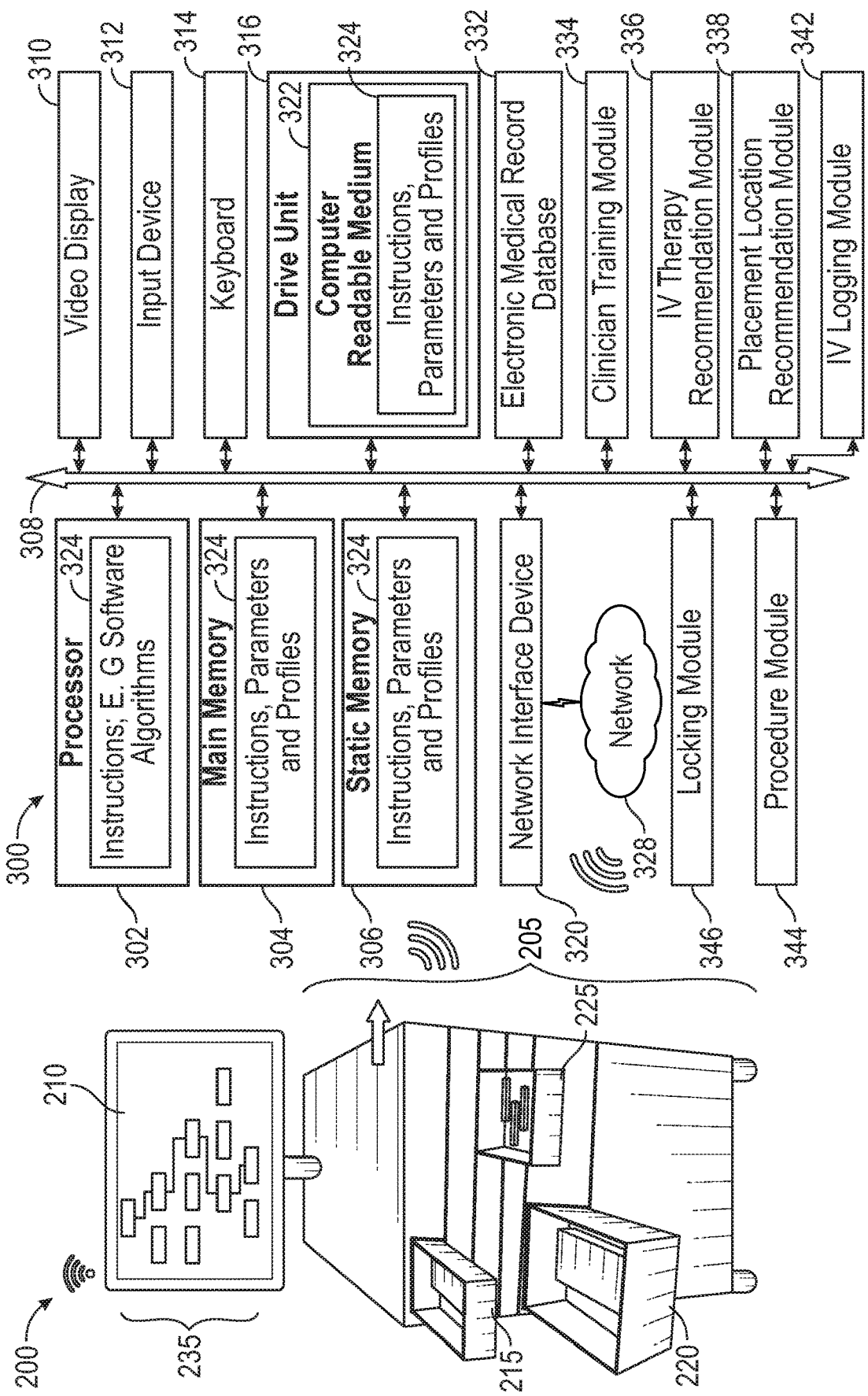
FIG. 3 is a graphical illustration of an intravenous therapy selection system and computing device communicatively coupled to the intravenous therapy selection system according to some embodiments of the present disclosure.

FIG. 3 is a graphical illustration of an intravenous therapy selection system 200 and computing device 300 communicatively coupled to the intravenous therapy selection system 200 according to some embodiments of the present disclosure. In the embodiments described herein, a computing device 300 includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. For example, the computing device 300 may be a personal computer, mobile device (e.g., personal digital assistant (PDA) or smart phone), server (e.g., blade server or rack server), a consumer electronic device, a network server or storage device, a network router, switch, or bridge, wireless router, or other network communication device, a network connected device (cellular telephone, tablet device, etc.), IoT computing device, wearable computing device, a set-top box (STB), a mobile information handling system, a palmtop computer, a laptop computer, a desktop computer, a communications device, an access point (AP), a base station transceiver, a wireless telephone, a land-line telephone, a control system, a camera, a scanner, a personal trusted device, a web appliance, the tablet 230 described in connection with FIG. 2, or any other suitable machine capable of executing a set of instructions (sequential or otherwise) that specify actions to be taken by that machine, and can vary in size, shape, performance, price, and functionality.

In a networked deployment, the computing device 300 may operate in the capacity of a server or as a client computer in a server-client network environment, or as a peer computer system in a peer-to-peer (or distributed) network environment. In a particular embodiment, the computing device 300 can be implemented using electronic devices that provide voice, video or data communication. For example, a computing device 300 may be any mobile or other computing device capable of executing a set of instructions (sequential or otherwise) that specify actions to be taken by that machine. Further, while a single computing device 300 is illustrated, the term "system" shall also be taken to include any collection of systems or sub-systems that individually or jointly execute a set, or multiple sets, of instructions to perform one or more computer functions.

The computing device 300 may include memory (volatile (e.g. random-access memory, etc.), nonvolatile (read-only memory, flash memory etc.) or any combination thereof), one or more processing resources, such as a central processing unit (CPU), a graphics processing unit (GPU), hardware or software control logic, or any combination thereof. Additional components of the computing device 300 may include one or more storage devices, one or more communications ports for communicating with external devices, as well as, various input and output (110) devices, such as a keyboard, a mouse, a video/graphic display, or any combination thereof. The computing device 300 may also include one or more buses 308 operable to transmit communications between the various hardware components. Portions of a computing device 300 may themselves be considered computing devices 300.

The computing device 300 can include devices or modules that embody one or more of the devices or execute instructions for the one or more systems and modules described herein, and operates to perform one or more of the methods described herein. The computing device 300 may execute code instructions 324 that may operate on servers or systems, remote data centers, or on-box in individual client information handling systems according to various embodiments herein. In some embodiments, it is understood any or all portions of code instructions 324 may operate on a plurality of computing devices 300.

The computing device 300 may include a processor 302 such as a central processing unit (CPU), control logic or some combination of the same. Any of the processing resources may operate to execute code that is either firmware or software code. Moreover, the computing device 300 may include memory such as main memory 304, static memory 306, computer readable medium 322 storing instructions 324 of the clinician training module 334, IV therapy recommendation module 336, placement location recommendation module 338, IV logging module 342, procedure module 344, locking module 346, and drive unit 316 (volatile (e.g. random-access memory, etc.), nonvolatile (read-only memory, flash memory etc.) or any combination thereof). The computing device 300 may also include one or more buses 308 operable to transmit communications between the various hardware components such as any combination of various input and output (I/O) devices.

The computing device 300 may further include a video display 310. The video display 310 in an embodiment may function as a liquid crystal display (LCD), an organic light emitting diode (OLED), a flat panel display, a solid-state display, or a cathode ray tube (CRT). Additionally, the computing device 300 may include an input device 312, such as a cursor control device (e.g., mouse, touchpad, or gesture or touch screen input, and a keyboard 314). In an embodiment, the video display 310 may include a touch screen that detects the touch of a clinician and interprets that input as described herein.

The network interface device shown as wireless adapter 320 can provide connectivity to a network 328, e.g., a wide area network (WAN), a local area network (LAN), wireless local area network (WLAN), a wireless personal area network (WPAN), a wireless wide area network (WWAN), or other networks. Connectivity may be via wired or wireless connection. The wireless adapter 320 may operate in accordance with any wireless data communication standards. To communicate with a wireless local area network, standards including IEEE 802.11 WLAN standards, IEEE 802.15 WPAN standards, WWAN such as 3GPP or 3GPP2, or similar wireless standards may be used. In some aspects of the present disclosure, one wireless adapter 320 may operate two or more wireless links. In the embodiments described herein, the network interface device 320 may wirelessly couple the computing device 300 with an intravenous therapy selection system 200. In the embodiments described herein, the intravenous therapy selection system 200 may receive data descriptive of a type of IV catheter to be used in a medical procedure and unlock and open any number of drawers 215, 220, and 225 to provide that IV catheter and any accompanying supplies.

In some embodiments, software, firmware, dedicated hardware implementations such as application specific integrated circuits, programmable logic arrays and other hardware devices can be constructed to implement one or more of some systems and methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by firmware or software programs executable by a controller or a processor system. Further, in an exemplary, non-limited embodiment, implementations can include distributed processing, component/object distributed processing, and parallel processing. Alternatively, virtual computer system processing can be constructed to implement one or more of the methods or functionalities as described herein.

The present disclosure contemplates a computer-readable medium that includes instructions, parameters, and profiles 324 or receives and executes instructions, parameters, and profiles 324 responsive to a propagated signal, so that a device connected to a network 328 can communicate voice, video or data over the network 328. Further, the instructions 324 may be transmitted or received over the network 328 via the network interface device or wireless adapter 320.

The computing device 300 may include a set of instructions 324 that can be executed to cause the computer system to perform any one or more of the methods or computer-based functions disclosed herein. For example, instructions 324 may execute a clinician training module 334, IV therapy recommendation module 336, placement location recommendation module 338, IV logging module 342, procedure module 344, and locking module 346 to engage in the functions of those various modules as described herein. Various software modules comprising application instructions 324 may be coordinated by an operating system (OS), and/or via an application programming interface (API). An example operating system may include Windows®, Android®, and other OS types. Example APIs may include Win 32, Core Java API, or Android APIs.

The disk drive unit 316 may include a computer-readable medium 322 in which one or more sets of instructions 324 such as software can be embedded. Similarly, main memory 304 and static memory 306 may also contain a computer-readable medium for storage of one or more sets of instructions, parameters, or profiles 324. The disk drive unit 316 and static memory 306 may also contain space for data storage. Further, the instructions 324 may embody one or more of the methods or logic as described herein. In a particular embodiment, the instructions, parameters, and profiles 324 may reside completely, or at least partially, within the main memory 304, the static memory 306, and/or within the disk drive 316 during execution by the processor 302 of computing device 300. As explained, some or all of the modules 334, 336, 338, 342, 344, and 346 may be executed locally or remotely. The main memory 304 and the processor 302 also may include computer-readable media.

Main memory 304 may contain computer-readable medium (not shown), such as RAM in an example embodiment. An example of main memory 304 includes random access memory (RAM) such as static RAM (SRAM), dynamic RAM (DRAM), non-volatile RAM (NV-RAM), or the like, read only memory (ROM), another type of memory, or a combination thereof. Static memory 306 may contain computer-readable medium (not shown), such as NOR or NAND flash memory in some example embodiments. The modules 334, 336, 338, 342, 344, and 346 may be stored in static memory 306, or the drive unit 316 on a computer-readable medium 322 such as a flash memory or magnetic disk in an example embodiment. While the computer-readable medium is shown to be a single medium, the term "computer-readable medium" includes a single-medium or multiple medium, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random-access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

The computing device 300 may also include the electronic medical record (EMR) database 332. The EMR database 332 may include one or more records of individual patient's receiving care or who have received care from a clinician or other HCP. In an embodiment, the sources of data to form the EMR database 332 may be accumulated at the computing device 300 from a plurality of sources interior and exterior to the computing device 300. These other sources exterior to the computing device 300 may include, for example, records maintained at another location (e.g., another hospital) where the patient received care. During operation of the computing device 300 and intravenous therapy selection system 200, a processor 302 may access this database in order to receive data describing past IV catheter use on the patient among other types of data used to form a decision tree 235 at the cart 205 or, in an embodiment, the video display 310 of the computing device 300.

The computing device 300 may also include the clinician training module 334. The clinician training module 334 may be executed by the processor 302 to receive data regarding certificates associated with the operating clinician and off-site and real scenario training the clinician has received. Additionally, the clinician training module 334 may access the EMR database 332 to determine the medical procedures the clinician has engaged in as well as the IV catheters used on various patients by the clinician. Self-reported levels of successfulness during the introduction of an IV catheter into a patient's body are also accessed. With this data accessed by the clinician training module 334, the decision tree 235 may be further augmented that may preselect certain decisions on the decision tree 235 based on the clinician's qualifications and past experience.

The computing device 300 may also include the IV therapy recommendation module 336. As described herein, the IV therapy recommendation module 336 may be executed by the processor 302 so as to form the decision tree 235 at the cart display device 210 or video display 310. Specifically, the IV therapy recommendation module 336 may iteravely aggregate a number of data sets from the EMR database 332, clinician training module 334, and placement location recommendation module 338 so as to create the various decisions of the decision tree 235 used by a clinician to come to a conclusion as to which IV catheter, among a plurality of IV catheters, to use on a patient and where to use that chosen IV catheter on the patient's body.

The computing device 300 may also include the placement location recommendation module 338. The placement location recommendation module 338 may also have access to a patient's records on the EMR database 332 and determine where on the patient's body the clinician is to introduce the IV catheter. The placement location recommendation module 338 may provide to the processor 302 data descriptive of the most optimal location to insert an IV catheter into the patient's body based on past use of an IV catheter on the patient and a reported level of successfulness of the placement. This information may be aggregated as described herein and reflected at the decision tree 235.

The computing device 300 may also include the IV logging module 342. The IV logging module 342 may receive input from the processor 302 initiated by the clinician that describes the use of a specific IV catheter on a patient. The IV logging module 342 may then update the EMR database 332 to reflect that the IV catheter was used on the patient as well as the location on the patient the IV catheter was used. The IV logging module 342 may also update an IV catheter stock database to reflect that the cart 205 no longer holds that IV catheter. In an embodiment, the IV logging module 342 may also provide alerts or emails indicating when the IV catheters and other stabilizing devices, flushes, dressings, and kits used to administer medical care on a patient should be replenished. As a consequence of executing the IV logging module 342 by the processor 302, the clinician may be made aware of the stock available within the cart 205 and may be directed to replenish any materials therein. Additionally, the IV logging module 342 may provide to the processor 302 information regarding the availability of use of any given IV catheter and notify the processor 302 that certain decisions on the decision tree 235 presented to the clinician are not available based on the availability of the IV catheters within the cart 205.

The computing device 300 may also include the procedure module 344. In an embodiment, the clinician may be made aware of how to proceed with the introduction of an IV catheter into a patient's body. For example, where the IV catheter suggested for use is not familiar to the clinician, the video display 310 of the computing device 300 may present, via execution of the procedure module 344, an audio and/or video presentation regarding how to administer the suggested IV catheter to the patient. This may allow the clinician to get on-site training regarding those IV catheters less familiar to the clinician. Additionally, the procedure module 344 may receive the clinician-reported description of the level of successfulness of the introduction of the IV catheter into the patient's body and may direct the clinician training module 334 to update the records associated with the clinician.

The computing device 300 may also include the locking module 346. The locking module 346 may be executed by the processor 302 to selectively allow and prevent access to any of the drawers 215, 220, and 225 within the cart 205. During operation of the computing device 300 and intravenous therapy selection system 200, the cart 205 may be locked so as to prevent access to the medical devices (e.g., the IV catheters and stabilizing devices, flushes, dressings, and kits used to administer medical care on a patient) maintained therein. Upon a clinician selecting an IV catheter on the decision tree 235 presented to the clinician on the cart display device 210 or video display 310, the locking module 346 may send a signal to the cart 205 to unlock those drawers 215, 220, and 225 that house the selected IV catheter and any accompanying stabilizing devices, flushes, dressings, and kits used to administer medical care on a patient. Additionally, the locking module 346 may determine whether credentials had been provided to the intravenous therapy selection system 200 or computing device 300 sufficient to allow access to the drawers 215, 220, and 225 at the cart 205. In an embodiment, the computing device 300 or intravenous therapy selection system 200 may include a near-field communication (NFC) receiver that detects the presence of a name tag or other security tag identifying a specific clinician and any accompanying access protocols used to access the drawers 215, 220, and 225 within the cart 205. Alternatively, the computing device 300 or intravenous therapy selection system 200 may include a security portal displayed on the video display 310 or cart display device 210 requesting a username and password required in order to gain access to the use of the intravenous therapy selection system 200 and computing device 300 as described herein.

The various modules 334, 336, 338, 342, 344, and 346 may be executed by the processor 302 either consecutively or concurrently in order to provide data to the clinician at the decision tree 235, receive input from the clinician, and execute their respective computer instructions in order to fulfill the functionalities of the intravenous therapy selection system 200 and computing device 300 as descried herein. In an embodiment, the modules 334, 336, 338, 342, 344, and 346 may be computer readable program code maintained on the memory 304 of the computing device 300. It is appreciated, however, that the computer readable program code defining the modules 334, 336, 338, 342, 344, and 346 may be maintained on any memory device at any computing device with the processor 302 accessing that code during operation of the computing device 300 and intravenous therapy selection system 200. In other embodiments, dedicated hardware implementations such as application specific integrated circuits, programmable logic arrays and other hardware devices can be constructed to for the modules 334, 336, 338, 342, 344, and 346 and implement the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit.

Accordingly, the present system encompasses software, firmware, and hardware implementations.

When referred to as a "system", a "device," a "module," a "controller," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCM-CIA) card, or other such expansion card), or a system (such as a motherboard, a system-on-a-chip (SoC), or a stand-alone device). The system, device, controller, or module can include software, including firmware embedded at a device, such as an Intel® Core class processor, ARM® brand processors, Qualcomm® Snapdragon processors, or other processors and chipsets, or other such device, or software capable of operating a relevant environment of the information handling system. The system, device, controller, or module can also include a combination of the foregoing examples of hardware or software. In an embodiment a computing device 300 may include an integrated circuit or a board-level product having portions thereof that can also be any combination of hardware and software. Devices, modules, resources, controllers, or programs that are in communication with one another need not be in continuous communication with each other, unless expressly specified otherwise. In addition, devices, modules, resources, controllers, or programs that are in communication with one another can communicate directly or indirectly through one or more intermediaries.

Although FIG. 3 shows that the computing device 300 and intravenous therapy selection system 200 are two separate physical devices, the present specification contemplates that the computing device 300 may form part of the intravenous therapy selection system 200 with the video display 310 of the computing device 300 being the cart display device 210. Alternatively, the computing device 300 described in connection with FIG. 3 may be in the form of a tablet device similar to the tablet 230 described in connection with FIG. 2.

Figure 4:
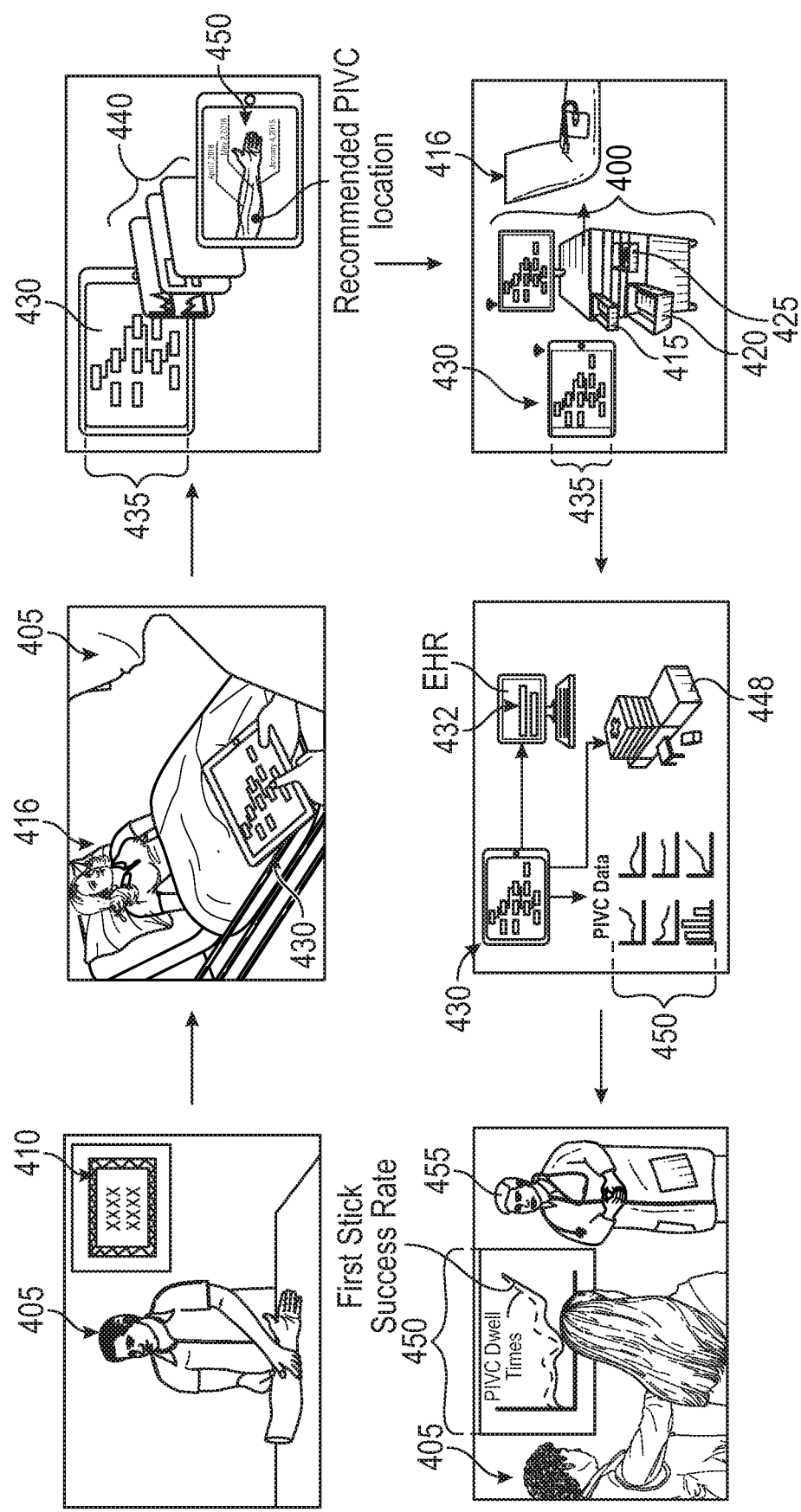
FIG. 4 is a flow diagram illustrating a method of operating an intravenous therapy selection system according to some embodiments of the present disclosure.

FIG. 4 is a flow diagram illustrating a method of operating an intravenous therapy selection system according to some embodiments of the present disclosure. The flow diagram may begin at the top left panel showing a clinician 405 engaged in practicing with and qualifying using an IV catheter on a medical model of an arm. During an initial set-up of the intravenous therapy selection system and computing device described herein, the clinicians may be tested for their use in IV catheter introduction in to a patient among other skills used to administer care to the patient. During this training process, a clinician 405 may receive certificates 410 indicating their qualifications to engage in certain medical activities. These qualifications may be IV catheter-specific qualifications or may be qualifications that allow or qualify the clinician 405 to use certain IV catheters on a patient and engage in other medical activities related to the patient. As described herein, the clinician training module 334 may receive input from a trainer or other superior indicating that a clinician 405 has or has not qualified to use certain IV catheters and engage in certain medical activities.

A top and center panel of FIG. 4 shows the clinician 405 operating the intravenous therapy selection system at a tablet computing device 430. The tablet computing device 430 may be similar to the computing device 300 described in connection with FIG. 3. In this panel, the clinician 405 may interact with a patient 416 to make certain selections on a decision tree presented to the clinician 405 on the tablet computing device 430. As described herein, the clinician 405 may make certain selections presented in order to identify an appropriate IV catheter to use on the patient based on the data received by the modules 334, 336, 338, 342, 344, and 346 described in connection with FIG. 3. In order to form the decision tree presented, the EMRs associated with the patient 416 and maintained on the EMR database may be accessed and processed in order to identify which of the IV catheters should be selected.

A right-most, top panel in FIG. 4 shows additional graphical illustrations 440 and 450 to the clinician descriptive of the data received from the EMR records associated with the patient 416. A specific graphical illustration includes a vascular scan 450 of the patient's 416 blood vessels. The vascular scan 450 may be a historical scan of the patient's veins or may be a real-time imaging of the blood vessels overlaid with historical markers indicating where, in the past, the patient 416 had received an IV catheter. The historical markers may be generated based on the EMRs of the patient 416 as well as the clinician-reported level of successfulness of the introduction of the IV catheters into the patient's body in the past. The other graphical illustrations 440 may be other medical records used by the clinician 405 to make an appropriate decision as to which of a plurality of IV catheters to use on the patient 416.

The flow diagram of FIG. 4 may continue at the right-most, bottom panel. Here the clinician 405 has made a decision as to which IV catheter to use and where to place that IV catheter using the decision tree presented to the clinician 405 on the tablet computing device 430. Upon selection of the IV catheter, the drawers 415, 420, and 425 on a cart 400 may be opened and the clinician 405 is given access to the IV catheter to administer it to the patient 416.

After the administration of the IV catheter, the flow diagram of FIG. 4 may move to the central, bottom panel. In this panel, a patient's 416 EMRs 432 are updated with IV catheter-related data 450 from the tablet computing device 430. This data may become part of the permanent medical history of the patient and may also be shared with other institutions 448 like other hospitals when appropriate and approved by the patient 416.

The bottom-most, left panel of FIG. 4 shows the clinician 405 engaging in a follow-up discussion regarding the clinician's 405 medical activities and may receive further training if necessary. Based on some analytics provided by the clinician training module 334, for example, an internal IV service or training and analytics team may identify and be guided to help the clinician 405 in improving the clinician's 405 use of certain IV catheters on patients 416 based on input received from the patients 416, the clinician 405 herself and other senior professionals. Here, the clinician 405 may be provided with training seminars to further perfect the clinician's 405 medical skills.

Figure 5:
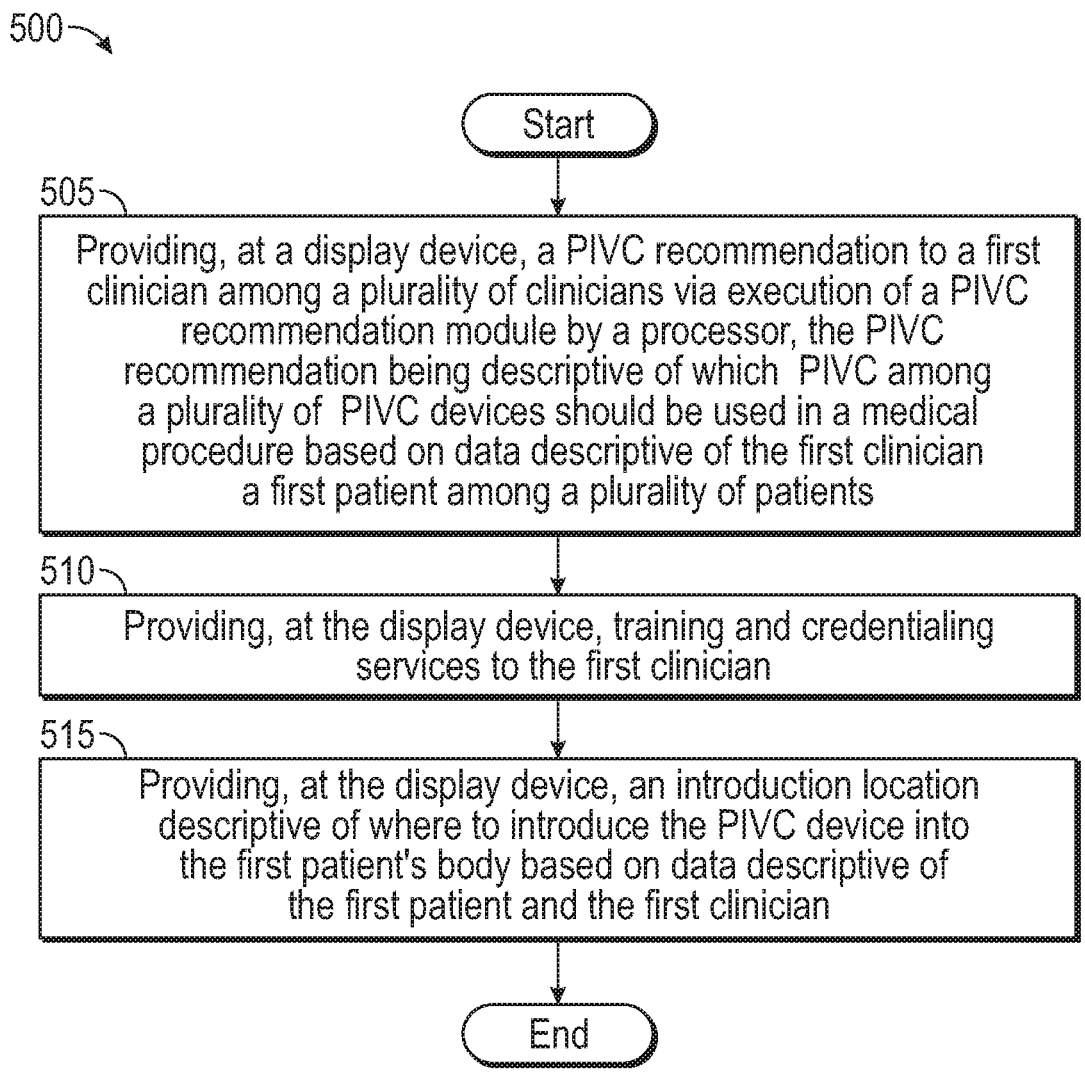
FIG. 5 is a flowchart depicting a method of recommending a peripheral intravenous catheter (PIVC) and introduction location according to some embodiments of the present disclosure.

FIG. 5 is a flowchart depicting a method 500 of recommending a peripheral intravenous catheter (PIVC) and introduction location according to some embodiments of the present disclosure. The method 500, at block 505, may include providing, at a display device, a PIVC recommendation to a first clinician among a plurality of clinicians via execution of a PIVC recommendation module by a processor. In this embodiment, the PIVC recommendation may be descriptive of which PIVC among a plurality of PIVC devices should be used in a medical procedure based on data descriptive of the first clinician and a first patient among a plurality of patients. By way of example, an EMR database may be accessed by a processor associated with the display device in order to provide patent-specific data related to a patient the PIVC is to be administered to. This data may include prior applications of PIVCs to the patient and their placement locations.

The method 500 may continue at block 510 with providing, at the display device, training and credentialing services to the first clinician. As described herein, the display device may present to the clinician a decision tree used by the clinician to come to an appropriate decision as to which PIVC to use on the patient. Among the decisions made on the decision tree may be the patient specific data as well as the data related to the qualifications of the clinician. In these embodiments, the use of certain PIVCs may be made unavailable to the clinician based on the lack of qualifications associated with the clinician at that time. Other PIVCs may, however, be chosen upon a determination at the decision tree that the clinician has been trained to use a specific PIVC.

The method 500 may also include, at block 515, providing, at the display device, an introduction location descriptive of where to introduce the PIVC device into the first patient's body based on data descriptive of the first patient and the first clinician. In this embodiment, the EMRs related to the patient may be accessed to determine where a PIVC has been administered to the patient's body as well as the successfulness of that administration. Additionally, past PIVC administration proficiency related to the clinician generally and at specific locations on a patient's body may be taken into consideration when providing the introduction location recommendation.

Figure 6:
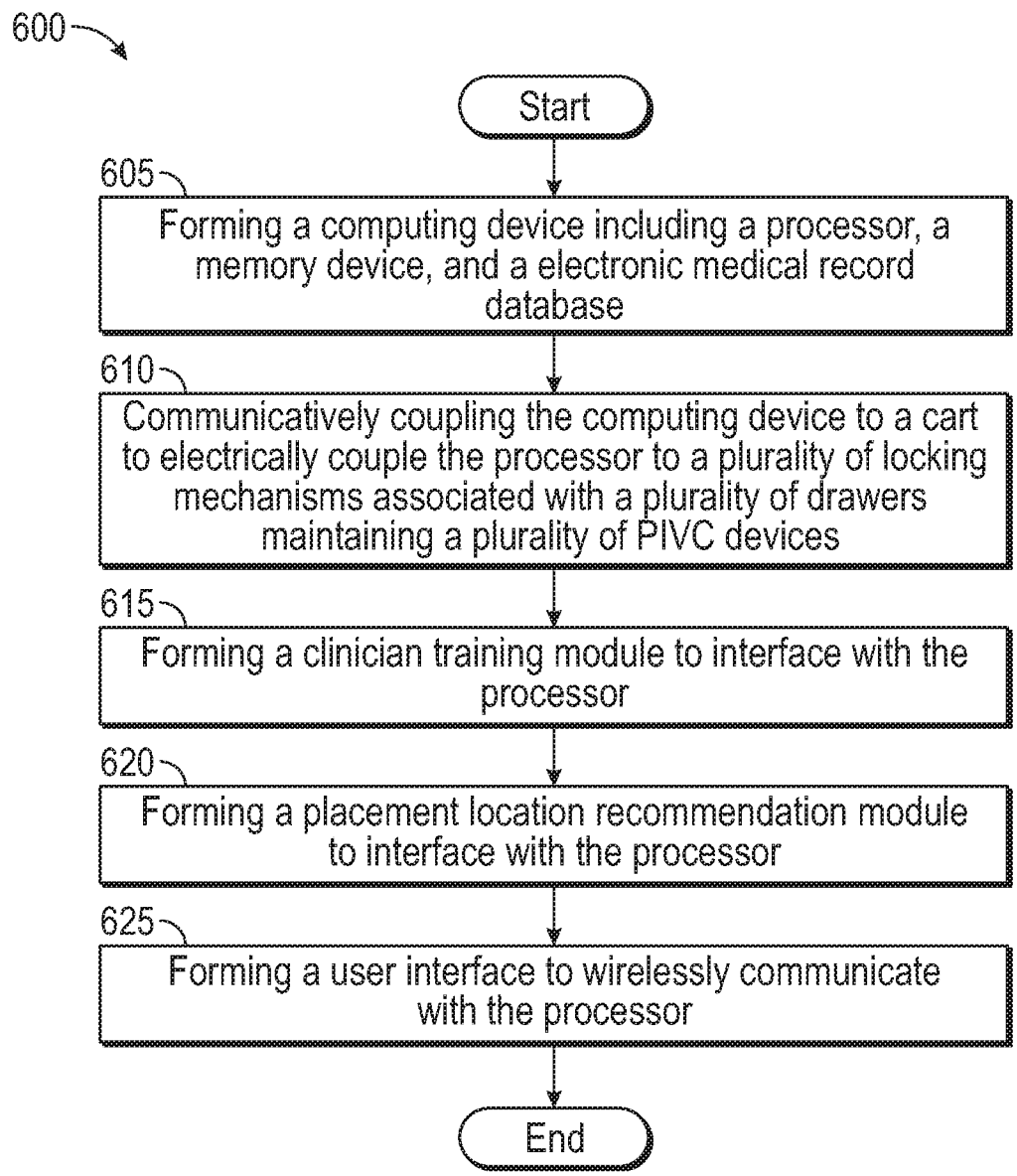
FIG. 6 is a flowchart depicting a method of manufacturing an intravenous therapy selection system according to some embodiments of the present disclosure.

FIG. 6 is a flowchart depicting a method 600 of manufacturing an intravenous therapy selection system according to some embodiments of the present disclosure. The method 600 may include, at block 605, forming a computing device including a processor, a memory device, and an electronic medical record database. The computing device may be any device that can access data at the EMR database and may, in an example, be remote to the EMR. In an embodiment, the computing device may be a plurality of computing devices used in cooperation to achieve the methods described herein.

The method 600 may include, at block 610, communicatively coupling the computing device to a cart to electrically couple the processor to a plurality of locking mechanisms associated with a plurality of drawers maintaining a plurality of PIVC devices. In this embodiment, the cart may maintain, physically, any PIVC and accompanying medical devices associated with the use of the PIVC.

The method 600 may continue at block 615 with forming a clinician training module to interface with the processor. The clinician training module may be executed by the processor to receive data regarding certificates associated with the operating clinician and off-site and real scenario training the clinician has received. Additionally, the clinician training module may access the EMR database to determine the medical procedures the clinician has engaged in as well as the IV catheters used on various patients by the clinician. Self-reported levels of successfulness during the introduction of an IV catheter into a patient's body are also accessed. With this data accessed by the clinician training module, the decision tree may be further augmented that may preselect certain decisions on the decision tree based on the clinician's qualifications and past experience.

The method 600 may also include, at block 620, forming a placement location recommendation module to interface with the processor. The placement location recommendation module may also have access to a patient's records on the EMR database and determine where on the patient's body the clinician is to introduce the IV catheter. The placement location recommendation module 338 may provide to the processor data descriptive of the most optimal location to insert an IV catheter into the patient's body based on past use of an IV catheter on the patient and a reported level of successfulness of the placement. This information may be aggregated as described herein and reflected at the decision tree.

The method 600 may also include, at block 625, forming a user interface to wirelessly communicate with the processor. As described herein, the user interface may include a video display that receives input from a clinician to determine which of a plurality of PIVCs to use and at what location on the patient's body. In order to more easily facilitate the decision process, a decision tree is presented on this display device that allows the user to make decisions based on an aggregation of data received from the EMR, received from a clinician training module, received from an PIVC recommendation module, received from a placement location recommendation module, and received from a PIVC logging module.

The embodiments described herein provide for an intravenous (IV) therapy selection system that uses patient EMR data and clinician data to identify appropriate PIVC to use and a location for the placement of selected PIVC. The systems and methods described herein, may prevent misuse of PIVCs by untrained clinicians while increasing the successfulness of PIVC administration to a patient. With the use of past EMR data, the system prevents damage to a patient's body where PIVCs had previously been administered to a patient. A decision tree may be provided to a clinician in order to determine the most appropriate PIVC to use at the most appropriate location on the patient. Training may be suggested and provided after use of the PIVC to the clinician and partially based on an assessment of the successfulness of the introduction of the PIVC into the patient's body. A PIVC cart may be provided to selectively secure the PIVCs therein until the clinician has made a decision on the appropriate PIVC and has provided security credentials to gain access to the PIVC.

Again, it is understood that the embodiments of the present application may be combined. As an example, the embodiments of FIGS. 1-6 may be arranged to fit specific uses based on the type of action being conducted. All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous (IV) therapy selection system, comprising:
   a cart having a plurality of drawers for holding different types of IV devices, the plurality of drawers being selectively locked;
   a processor that is integrated with the plurality of drawers of the cart, the processor being configured to selectively open the plurality of drawers;
   a memory device that is integrated with the processor and stores an electronic medical record database comprising a plurality of medical records related to a plurality of patients, the memory device also storing an IV therapy recommendation module, and a placement location recommendation module; and a display device integrated into or with the cart, the display device being configured to provide, using the IV therapy recommendation module, an IV device recommendation based on data descriptive of a first patient and a first clinician who is caring for the first patient, the display device further being configured to provide, using the placement location recommendation module, a recommendation on where to introduce the IV device into the first patient's body based on the data descriptive of the first patient and the first clinician;

wherein the IV therapy recommendation module is configured to generate the IV device recommendation by performing the following:

receiving patient identification information for the first patient;

in response to receiving the patient identification information for the first patient, accessing the plurality of medical records to determine whether the plurality of medical records include a medical record that is associated with the received patient identification information;

presenting a decision tree to the first clinician, wherein when the plurality of medical records include a medical record that is associated with the received patient identification information, the decision tree is presented with one or more preliminary decisions selected including a preliminary decision identifying a particular blood vessel to select, whereas when the plurality of medical records do not include a medical record that is associated with the received patient identification information, the decision tree is not presented with any preliminary decisions selected;

receiving an identifier of the first clinician;

in response to receiving the identifier of the first clinician, customizing the decision tree based on performance data of the first clinician including one or more of including options in the decision tree for using one or more IV devices or removing one or more options in the decision tree for using one or more other IV devices;

receiving, from the processor, an indication of IV devices that are contained in the cart;

in response to receiving, from the processor, the indication of IV devices that are contained in the cart, further customizing the decision tree;

after presenting and customizing the decision tree, receiving input from the first clinician to override the decision tree; and in response to the input, selecting and providing the IV device recommendation;

wherein, after the display device provides the IV device recommendation and the first clinician selects the first type of IV device, the processor opens a first drawer of the plurality of drawers based on the first clinician's selection of the first type of IV device provided by display device using the IV therapy recommendation module, the first drawer storing the first type of IV device, to thereby allow the first clinician to obtain the first type of IV device.

2. The intravenous therapy selection system of claim 1, wherein the cart further comprises an input device to receive input from the first clinician to record the use of the first type of IV device and a location on the first patient's body where the first clinician inserted the first type of IV device.

3. The intravenous therapy selection system of claim 1, wherein the cart further comprises an input device to receive input from the first clinician to record a level of successfulness of the introduction of the first type of IV device into the first patient's body.

4. The intravenous therapy selection system of claim 3, further comprising a module to provide the first clinician with procedures descriptive of how to better introduce the first type of IV device into a subsequent patient based on the recorded level of successfulness of the introduction of the first type of IV device into the first patient's body.

5. The intravenous therapy selection system of claim 1, further comprising a procedure module to provide the first clinician with directions regarding how to introduce the first type of IV device into the first patient's body.

6. The intravenous therapy selection system of claim 1, further comprising a locking module to mechanically lock the plurality of drawers of the cart.

7. The intravenous therapy selection system of claim 1, further comprising an IV logging module to track the use, stocking, and depletion of the different types of IV devices held in the plurality of drawers of the cart.

8. The intravenous therapy selection system of claim 1, wherein the display device is integrated into the cart.

9. The intravenous therapy selection system of claim 1, wherein the display device is separate from the cart.

10. The intravenous therapy selection system of claim 9, wherein the display device includes a module for communicating with the processor to cause the processor to open the plurality of drawers.

11. An intravenous (IV) therapy selection system, comprising:

a processor that is integrated with a plurality of drawers of a cart, the processor being configured to selectively open the plurality of drawers;

the cart having the plurality of drawers, each of the plurality of drawers storing a different type of IV catheter, the cart including a locking module for selectively locking each of the plurality of drawers, wherein the cart also includes one or more additional drawers storing one or more of stabilizing devices, flushes, dressings, or kits; and a display device having one or more modules for presenting, to a clinician, patient information for a patient and performance information of the clinician;

wherein the one or more modules are configured to receive input from the clinician while the clinician cares for the patient and, in response to the input, identify a first type of IV catheter that is recommended for the clinician to insert into the patient, wherein the one or more modules identify the first type of IV catheter that is recommended by performing the following:

receiving patient identification information for the patient;

in response to receiving the patient identification information for the patient, accessing a plurality of medical records to determine whether the plurality of medical records include a medical record that is associated with the received patient identification information;

presenting a decision tree to the clinician, wherein when the plurality of medical records include a medical record that is associated with the received patient identification information, the decision tree is presented with one or more preliminary decisions selected including a preliminary decision identifying a particular blood vessel to select, whereas when the plurality of medical records do not include a medical record that is associated with the received patient identification information, the decision tree is not presented with any preliminary decisions selected;

receiving an identifier of the clinician;

in response to receiving the identifier of the clinician, customizing the decision tree based on performance data of the clinician including one or more of including options in the decision tree for using one or more IV catheters or removing one or more options in the decision tree for using one or more other IV catheters;

receiving, from the processor, an indication of IV catheters that are contained in the cart;

in response to receiving, from the processor, the indication of IV catheters that are contained in the cart, further customizing the decision tree;

after presenting and customizing the decision tree, receiving input from the clinician to override the decision tree; and in response to the input, selecting and recommending the first type of IV catheter;

wherein after the one or more modules identify the first type of IV catheter and the clinician selects the first type of IV catheter, the processor unlocks a first drawer of the plurality of drawers based on the clinician's selection of the first type of IV catheter identified by the one or more modules, the first drawer storing the first type of IV catheter, to thereby allow the clinician to obtain the first type of IV catheter to insert into the patient, and wherein after the one or more modules identify the first type of IV catheter and the clinician selects the first type of IV device, the processor unlocks a second drawer of the plurality of drawers, the second drawer storing a flush device, and wherein after the one or more modules identify the first type of IV catheter and the clinician selects the first type of IV device, the processor unlocks a third drawer of the plurality of drawers, the third drawer storing a start kit comprising a stabilizing device and a swab.

12. The IV therapy selection system of claim 11, wherein the display device is integrated into the cart.

13. The IV therapy selection system of claim 11, wherein the one or more modules are configured to recommend a location on the patient's body where the first type of IV catheter should be inserted.

14. The IV therapy selection system of claim 11, wherein the one or more modules are configured to receive input from the clinician identifying a location on the patient's body where the clinician inserted the first type of IV catheter.

15. The IV therapy selection system of claim 11, wherein the patient information for the patient identifies which types of IV catheters were previously inserted into the patient's body.

16. The intravenous therapy selection system of claim 1, wherein the display device is configured to provide the first type of IV device such that the first clinician selects the first type of IV device on the display device.

17. The IV therapy selection system of claim 1, wherein customizing the decision tree based on performance data of the first clinician comprises including options in the decision tree for using one or more IV devices based on determining that the first clinician has been trained to use the one or more IV devices.

18. The IV therapy selection system of claim 1, wherein customizing the decision tree based on performance data of the first clinician comprises including options in the decision tree for using one or more IV devices based on determining that the first clinician has previously used the one or more IV devices successfully.

19. The IV therapy selection system of claim 1, wherein the cart includes a near-field communication (NFC) receiver and the identifier of the first clinician is received via the NFC receiver.

* * * * *